(12) United States Patent
Lewis (10) Patent No.: US 8,491,484 B2
(45) Date of Patent: Jul. 23, 2013

(54) FORWARD LOOKING IMAGING GUIDEWIRE

(75) Inventor: Nickola Lewis, Fremont, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1740 days.

(21) Appl. No.: 11/104,865

(22) Filed: Apr. 12, 2005

(65) Prior Publication Data

US 2006/0241478 A1 Oct. 26, 2006

(51) Int. Cl.
*A61B 8/14* (2006.01)

(52) U.S. Cl.
USPC ........... 600/466; 600/459; 600/462; 600/467; 600/469; 600/472

(58) Field of Classification Search
USPC ................. 600/407, 440, 462, 470, 471, 459, 600/466, 46, 469, 472
See application file for complete search history.

(56) References Cited

U.S. PATENT DOCUMENTS

| | | | |
|---|---|---|---|
| 4,576,177 A | | 3/1986 | Webster, Jr. |
| 5,203,337 A | * | 4/1993 | Feldman ........................ 600/463 |
| 5,235,964 A | * | 8/1993 | Abenaim ........................ 600/139 |
| 5,368,035 A | | 11/1994 | Hamm et al. |
| 5,373,845 A | | 12/1994 | Gardineer et al. |
| 5,373,849 A | | 12/1994 | Maroney et al. |
| 5,379,772 A | | 1/1995 | Imran |
| 5,464,016 A | | 11/1995 | Nicholas et al. |
| 5,779,643 A | | 7/1998 | Lum et al. |
| 5,925,016 A | * | 7/1999 | Chornenky et al. ........ 604/96.01 |
| 6,200,269 B1 | | 3/2001 | Lin et al. |
| 6,241,744 B1 | * | 6/2001 | Imran et al. .................... 606/159 |
| 6,459,921 B1 | | 10/2002 | Belef et al. |
| 6,481,439 B1 | * | 11/2002 | Lewis et al. .................... 128/898 |
| 6,485,413 B1 | * | 11/2002 | Boppart et al. ................ 600/160 |
| 6,529,760 B2 | * | 3/2003 | Pantages et al. ............... 600/407 |
| 2003/0130657 A1 | * | 7/2003 | Tom et al. ........................ 606/47 |

FOREIGN PATENT DOCUMENTS

| | | |
|---|---|---|
| GB | 2313668 | 12/1997 |
| JP | H-07-003608 | 1/1995 |
| JP | H-07-124164 | 5/1995 |
| JP | H-08-335635 | 12/1996 |
| WO | 99/49910 | 10/1999 |
| WO | 0035349 A1 | 6/2000 |
| WO | WO 00/35349 A | 6/2000 |

\* cited by examiner

*Primary Examiner* — Long V. Le
*Assistant Examiner* — Ellsworth Weatherby
(74) *Attorney, Agent, or Firm* — Frommer Lawrence & Haug LLP; Patrick R. Turner (57) ABSTRACT

The systems and methods described herein provide for a forward looking guidewire having a reduced radial cross-section for increased maneuverability and use of the guidewire within more narrow vasculature. The guidewire can include an elongate tubular member having a distal region, proximal region and inner lumen and a forward looking imaging device coupled with the distal end of the guidewire. The distal region of the guidewire can be relatively more flexible than the proximal region. The guidewire can also include a second, side looking imaging device, which can be coupled around a longitudinal portion of the guidewire in the radial or proximal regions.

40 Claims, 9 Drawing Sheets

FORWARD LOOKING IMAGING GUIDEWIRE

FIELD OF THE INVENTION

The field of the invention relates generally to a guidewire having forward looking capability for use in medical imaging.

BACKGROUND INFORMATION

Conventional medical imaging systems used in the imaging of blood vessel interiors typically include a guidewire and a catheter. The guidewire is usually inserted into the blood vessel and then advanced to the area of interest using an external imaging technique such as fluoroscopy. Once in place, the catheter is routed over the guidewire and into proximity with the area of interest, which may be a diseased tissue region such as a blood vessel occlusion or plaque, a deployed interventional device such as a stent, or any other area of interest. The catheter can include one or more imaging devices for imaging the area of interest. The catheter can also be configured to perform one or more interventional therapies to the area of interest. Typical imaging catheters have forward looking and/or side looking imaging capabilities, i.e., the catheter is capable of imaging a region distal to the catheter and/or a region along side a longitudinal axis of the catheter, respectively. Typical interventional therapies include tissue ablation, drug delivery or the use of an interventional device such as a balloon or a stent, etc.

Before administering an interventional therapy, it is desirable to obtain an image of the area of interest to locate, for instance, the diseased tissue and characterize the tissue type so that the proper interventional therapy can be chosen and administered. This is commonly performed with the aid of an imaging catheter. In cases where the blood vessel is weakened or in an serious disease state, advancement of the catheter into proximity with the diseased tissue increases the risk of the blood vessel being injured or ruptured. This risk is even greater when operating within narrow vasculature having thin vessel walls that are more susceptible to injury.

Accordingly, there is a need for smaller intravascular imaging systems capable of imaging within narrow vasculature with a reduced risk of injury.

SUMMARY

The systems and methods described herein provide for a guidewire having forward looking capability. In one example embodiment, the guidewire can include an elongate tubular member having a distal region, a proximal region and an inner lumen where the width, or diameter, of the distal region is substantially 0.025 inches or less. The guidewire can also include an imaging device configured to image a region located at least partially distal to the elongate tubular member. In another embodiment, the guidewire can include an imaging device and an elongate tubular member having a distal region, a proximal region and an inner lumen, where the imaging device has a first surface coupled with the distal region of the elongate tubular member and is configured to image a region located at least partially distal to the elongate tubular member.

The imaging device can be located within the inner lumen and coupled with a distal end of the tubular member. For instance, in one embodiment the distal region is relatively more flexible than the proximal region and includes a sonolucent distal end section with the imaging device coupled thereto. The imaging device can be coupled with the sonolucent end section via an adhesive, and the adhesive and sonolucent end section can each be separately configured as matching layers for the imaging device, for use with imaging techniques which are amenable to matching layers, such as ultrasound imaging, etc. The guidewire can also include an imaging device configured to provide side looking capability. In one embodiment, the guidewire includes an imaging device coupled radially about a longitudinal portion of the elongate tubular member.

Also provided is a method of imaging with a forward looking guidewire. In one example, the method can include inserting a guidewire into a blood vessel of a living being, where the guidewire includes an imaging device having a width that is substantially 0.025 inches or less, and then imaging a region of the blood vessel located at least partially distal to the guidewire with the imaging device. The method can also include determining the range to an area of interest located within the imaged region or characterizing the area of interest. A catheter can be advanced over the guidewire to the area of interest, where the catheter can be used to image the area of interest or to perform an interventional therapy. The guidewire can be used to image the area of interest during and/or after the interventional therapy, with either the forward looking imaging device or with a second, side looking imaging device.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments. The figures are not to scale and the size of the features in relation to each other is not intended to limit the invention in any way.

DETAILED DESCRIPTION

Figure 1:
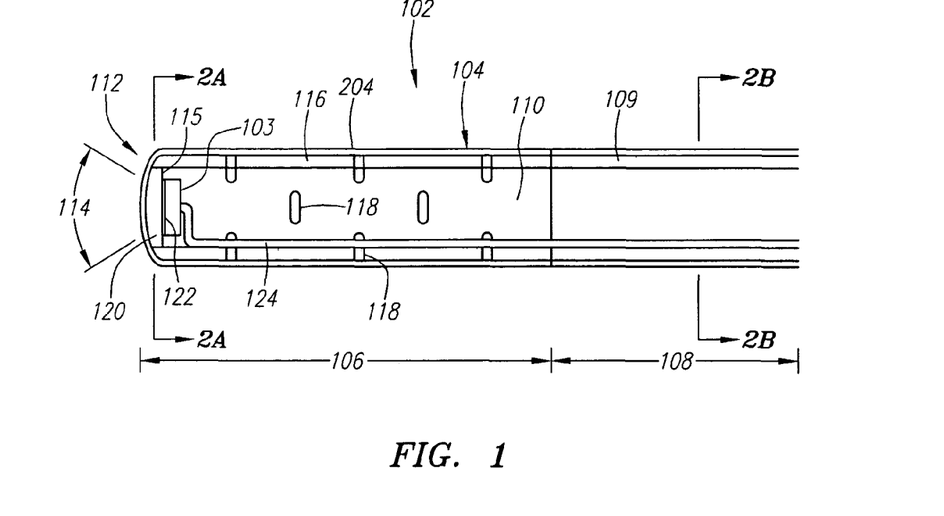
FIG. 1 is a schematic view depicting an example embodiment of a forward looking guidewire.

The medical systems and methods described herein provide for a guidewire having forward looking capability. FIG. 1 depicts an example embodiment of forward looking guidewire 102. Guidewire 102 includes imaging device 103 and elongate tubular member 104, which has distal region 106, proximal region 108 and inner lumen 110. Imaging device 103 is coupled with distal end 112 of member 104 and configured to image a forward region 114 located at least partially distal to distal end 112 of member 104. This forward looking capability allows a physician or other user to image the interior of a blood vessel prior to advancing an imaging catheter into or near to the area of interest. As will be explained with reference to FIGS. 2A-B, guidewire 102 also has a reduced width in the radial direction, which translates to a reduced radial cross-sectional area. This can allow guidewire 102 to achieve numerous advantages over conventional guidewires such as, for example, increased maneuverability and the ability to operate within much more constricting vasculature.

Distal region 106 of elongate tubular member 104 is preferably relatively more flexible than proximal region 108. In this embodiment, distal region 106 includes a tubular floppy section 116 having a plurality of apertures 118 for added flexibility. Floppy section 116 is preferably metallic, but can be composed of any flexible material according to the needs of the application.

In this embodiment, imaging device 103 is an ultrasound imaging device such as a single element transducer or transducer array, although imaging device 103 can also be a light-based optical imaging device (such as one that relies on optical coherence tomography or OCDR) or any other type of imaging device. Based on the configuration of imaging device 103, forward imaging region 114 can be as broad, focused, shallow or deep as desired. Imaging device 103 can communicate with external imaging system 806 (depicted in FIG. 8) over signal line 124. Signal line 124 can include as many separate communication channels as needed by imaging device 103. For instance, in embodiments where imaging device 103 is a transducer array having N transducer connections, signal line 124 can also include N separate communication channels.

Imaging device 103 can be placed at any orientation or at any position in distal region 106 that allows the imaging of forward region 114. In this embodiment, imaging device 103 is coupled with sonolucent end section 120, which, in turn is coupled with floppy section 116 at distal end 112. Here, sonolucent end section 120 has a cap-like shape and provides a window through which imaging device 103 can image. In this embodiment, sonolucent end section 120 is composed of a polymer, although any sonolucent material can be used. The amount of ultrasound energy attenuated by sonolucent end section 120 is preferably minimal, but is dependent upon the needs of the application.

Imaging device 103 can be coupled with end section 120 in any manner in accordance with the needs of the application, including the use of thermal bonding, adhesives, encapsulation and the like. Imaging device 103 is preferably bonded to end section 120 with an adhesive gel 122, although any type of adhesive can be used. Adhesive gel 122 and/or sonolucent end section 120 can each be configured as a matching layer for imaging device 103 to increase the performance characteristics of imaging device 103.

Figure 2A:
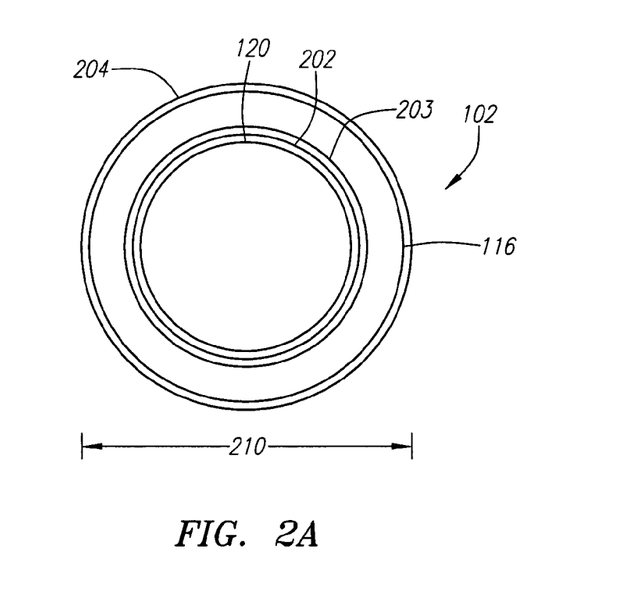
FIG. 2A is a cross-sectional view depicting an example radial cross-section of the forward looking guidewire of FIG. 1 taken over line 2A-2A.
Figure 2B:
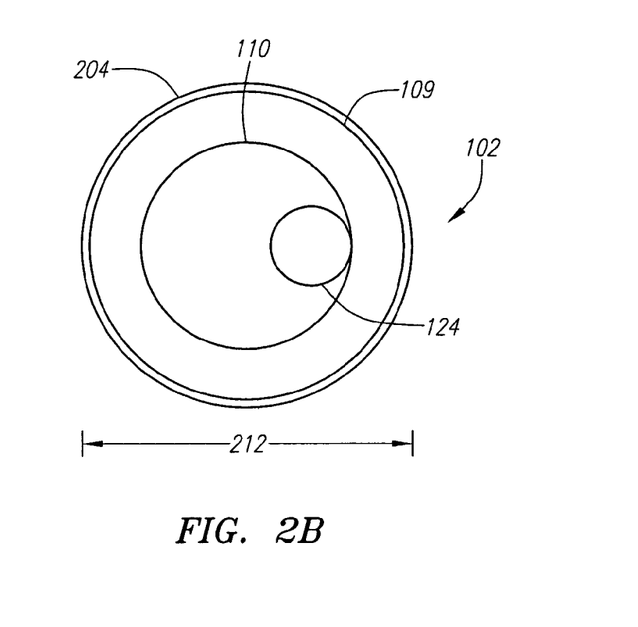
FIG. 2B is a cross-sectional view depicting an example radial cross-section of the forward looking guidewire of FIG. 1 taken over line 2B-2B.

FIGS. 2A-B are cross-sectional views of guidewire 102 where FIG. 2A is taken along line 2A-2A of FIG. 1 and FIG. 2B is taken along line 2B-2B of FIG. 1. In FIG. 2A, end section 120 is adhesively bonded to metallic floppy section 116 using adhesive layer 202, although any coupling technique can be used. Floppy section 116 can optionally include an inner polymer layer 203 to cover the inner metallic surface. This inner polymer layer 203 can be omitted where end section 120 is bonded with floppy section 116 if desired. Floppy section 116 can also include one or more outer layers 204. Outer layer 204 is preferably a polymer layer for added lubricity while operating within the blood vessel. Outer layer 204 can also include a medicinal agent in addition to, or in place of the polymer layer. The medicinal agent can be any desired agent or drug. For instance, in one embodiment, outer layer 204 includes a thrombolytic agent for aid in treating a blood vessel occlusion.

In FIG. 2B, proximal tubular section 109 is also covered with outer layer 204 but inner layer 203 is optionally omitted. Proximal tubular section 109 can be configured in any manner in accordance with the needs of the application. For instance, proximal tubular section 109 can be a polymer tube, metallic hypotube etc. Proximal section 109 can be configured with a plurality of apertures that communicate with the vascular system, allowing flushing, or reception of blood within the shaft for improved imaging. Signal line 124 can also be coupled with inner surface 126 of tubular section 109 if desired.

Guidewire 102 has reduced widths 210 and 212 as shown in the radial cross-sections of FIGS. 2A-B, respectively. In distal region 106, guidewire 102 preferably has a maximum width 210 of substantially 0.035 inches or less. Width 212 in proximal region 108 can be greater than the width 210 of distal region 106 if desired, although both width 210 and 212 are preferably minimized. In one embodiment, widths 210 and 212 are both substantially 0.025 inches or less. In another embodiment, widths 210 and 212 are substantially 0.018 inches. As used herein with regard to widths 210 and 212, the term "substantially" is intended to convey that the recited value need not be limited to that value precisely and that the recited value is not limited only to those widths which result in the recited value after rounding.

Figure 3:
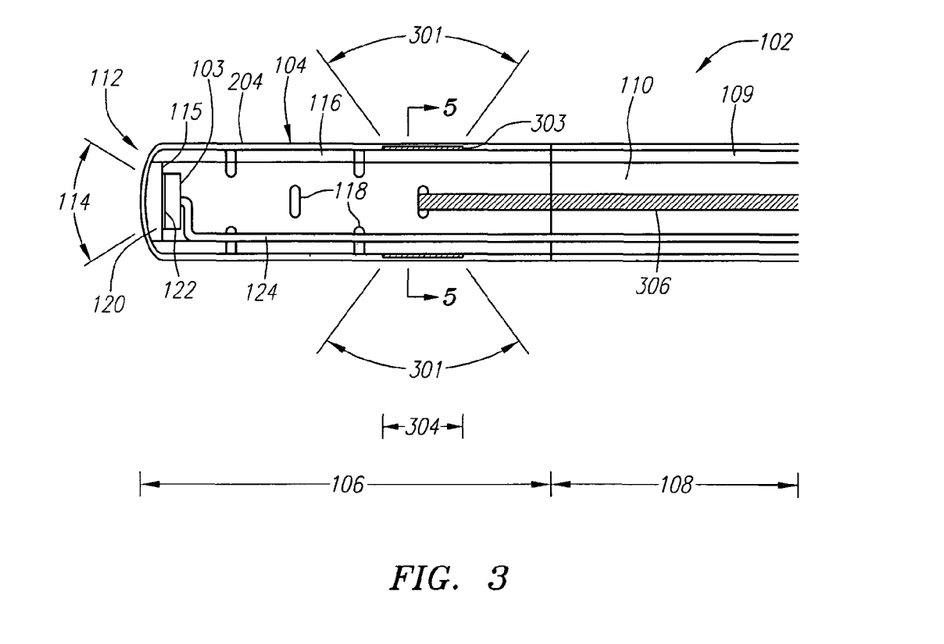
FIG. 3 is a schematic view depicting an example embodiment of a guidewire having both forward looking and side looking capability.
Figure 4A:
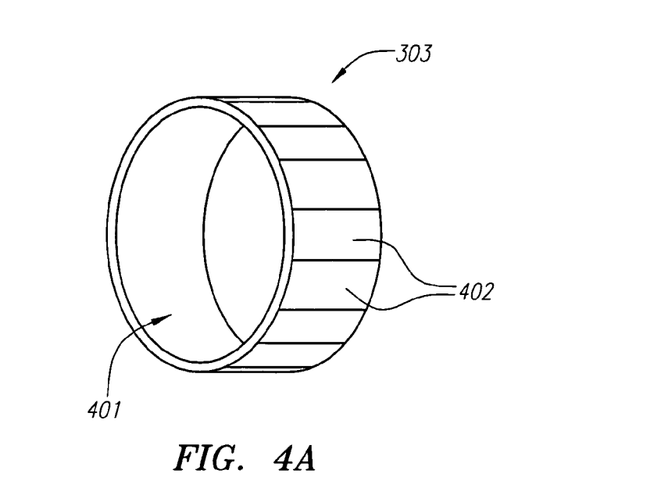
FIGS. 4A-B are perspective views depicting example embodiments of side looking imaging devices.
Figure 4B:
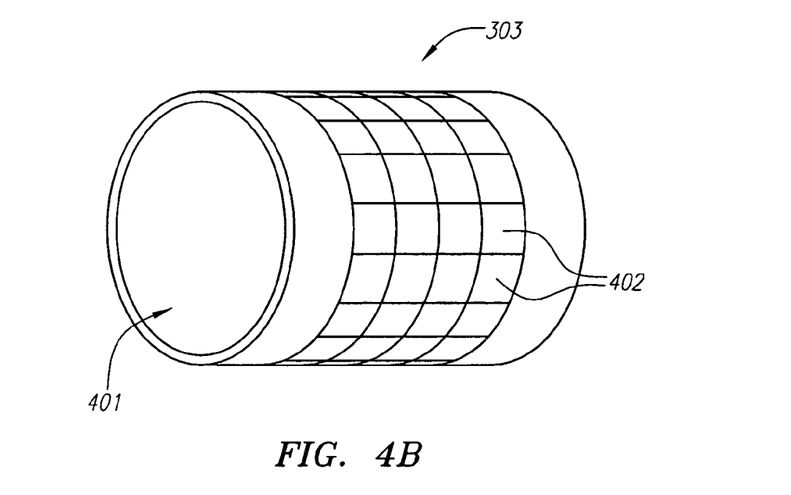

FIG. 3 is a schematic view depicting another example embodiment of guidewire 102. In this embodiment, guidewire 102 has a second imaging device 303 configured to provide guidewire 102 with side looking capability over region 301. Imaging device 303 is preferably a transducer array coupled radially about a longitudinal section 304 of elongate member 104. Imaging device 303 is preferably shaped to conform to the shape and/or contours of elongate tubular member 104. Based on the configuration of imaging device 303, side imaging region 301 can be as broad, focused, shallow or deep as desired. In this embodiment, imaging device 303 is substantially cylindrical. As used herein with respect to imaging device 303, the term "substantially" is intended to convey that imaging device 303 is not limited to imaging devices that are perfectly or even mostly cylindrical. FIGS. 4A-B are perspective views depicting example embodiments of cylindrical imaging device 303 with an open inner section 401. FIG. 4A depicts cylindrical imaging device 303 as an array with a single row of transducer elements 402 arranged around the circumference of imaging device 303. FIG. 4B depicts cylindrical imaging device 303 as a phased array having rows and columns of transducer elements 402 arranged around the circumference of imaging device 303. Imaging device 303 can include any number of elements 402 arranged in any number of rows and columns. Furthermore, imaging device 303 is not limited to phased array devices or other ultrasound devices.

Figure 5:
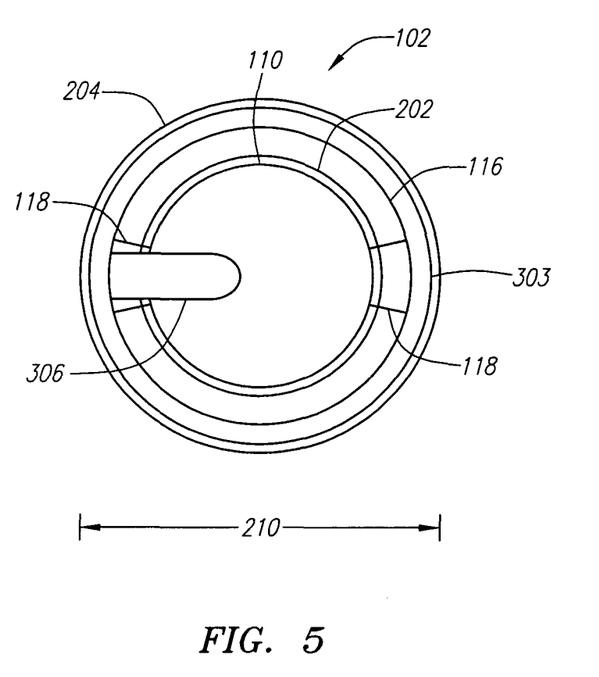
FIG. 5 is a schematic view depicting an additional example embodiment of the guidewire having both forward looking and side looking capability.

Referring back to FIG. 3, imaging device 303 is preferably placed in or near distal region 106. Here, imaging device 303 is placed outside of floppy section 116 and is communicatively coupled with the imaging system via signal line 306, which is routed from within inner lumen 110 to imaging device 303 through one or more apertures 118, as shown in FIG. 5, which is a cross-sectional view depicting an example embodiment of guidewire 102 taken along line 5-5, which is distal to proximal region 108. Here, signal line 306 is coupled with imaging device 303 through aperture 118. Imaging device 303 is also preferably covered with outer layer 204, which is preferably a sonolucent layer such as a polymer etc.

Figure 6A:
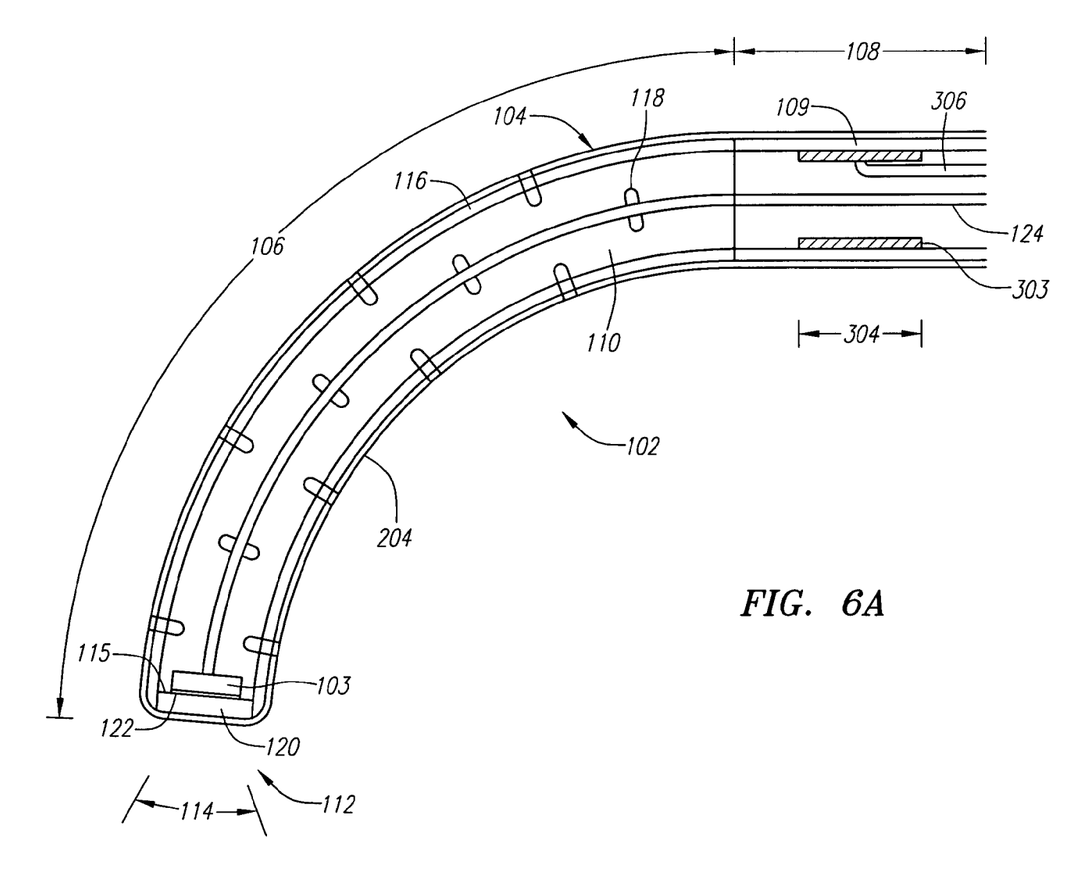
FIGS. 6A-B are schematic views depicting additional example embodiments of the guidewire having both forward looking and side looking capability.
Figure 6B:
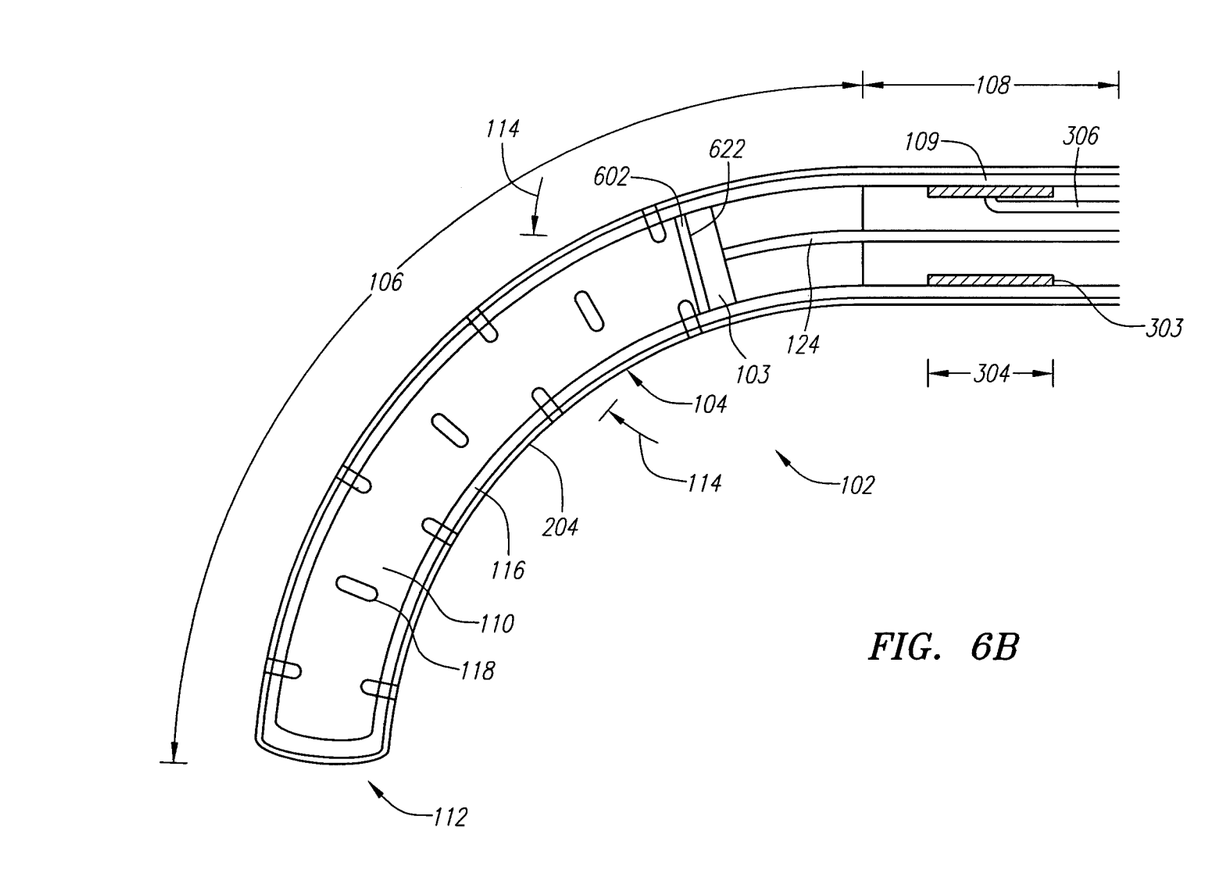

Imaging device 303 can also be placed in proximal section 108 if desired. FIG. 6A depicts an example embodiment of guidewire 102 with imaging device 303 located within inner lumen 110 of member 104 in proximal region 108 near distal region 106. In this embodiment, floppy section 116 is curved to facilitate navigation of guidewire 102 through the vasculature of the patient. FIG. 6B depicts another example embodiment of guidewire 102 with imaging device 303, except in this embodiment, imaging device 103 is located at a position more proximal to distal end 112 than in the embodiment depicted in FIG. 6A. While depicted as being within the curved portion of distal region 106, imaging device 103 can also be placed in the relatively straighter portion located proximal to the curved portion. This allows for imaging device 103 to image through bends in guidewire 102. For instance, imaging device 103 can image a Chronic Total Occlusion (CTO) originating at a bifurcation in the blood vessel, while maintaining the position of guidewire 102 within the vessel. In this embodiment, imaging device 103 is coupled with a sonolucent section 602, which preferably extends radially across inner lumen 110 and provides support for imaging device 103. Placement of imaging device 103 in the more proximal position allows imaging device 103 to image a more proximal region 114 than that depicted in FIG. 6A.

In this embodiment, floppy section 116 is preferably composed of a sonolucent material to allow imaging device 103 to obtain images through section 116, which, as mentioned above, can be relatively straight or curved. Imaging device 103 can be coupled with sonolucent section 602 via an adhesive layer 622 and, similar to embodiments described above, both sonolucent section 602 and adhesive layer 622 can be configured as matching layers. In another embodiment, sonolucent section 622 can be omitted and imaging device 103 can be coupled with the inner surface of elongate member 104 directly using, for instance, an adhesive placed around the circumference or perimeter of imaging device 103. One of skill in the art will readily recognize that imaging device 103 and sonolucent section 602, if present, can be placed at any position within guidewire 102.

Figure 7A:
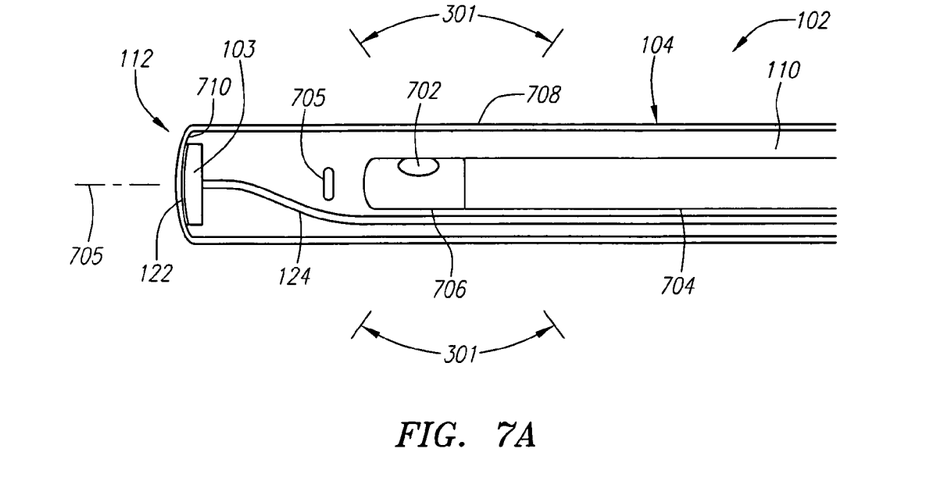
FIGS. 7A-B are schematic views depicting additional example embodiments of the guidewire having both forward looking and side looking capability.

FIG. 7A depicts another example embodiment of guidewire 102 with side looking capability. In this embodiment, a single element transducer 702 is coupled with rotatable driveshaft 704 located within inner lumen 110. Single element transducer 702 can be mounted in housing 706 or mounted directly to driveshaft 704. Side looking capability is provided by operating transducer 704 during concurrent rotation of driveshaft 704 to image multiple positions about rotational axis 705. Also depicted is vent aperture 705, which can be used to provide fluid communication between lumen 110 and the exterior environment. In this embodiment, floppy section 116 has been optionally omitted and elongate tubular member 104 is a continuous polymer tube 708 with imaging device 103 coupled with the inner surface 710 thereof.

Figure 7B:
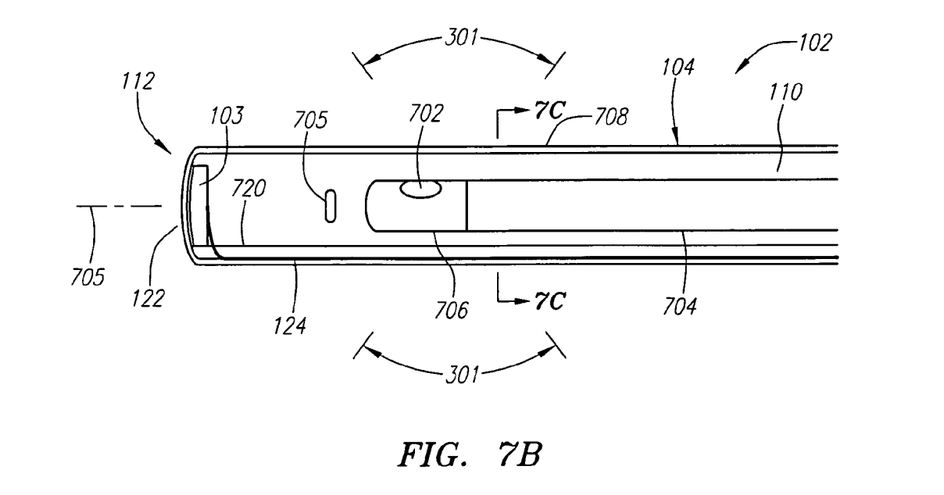

FIG. 7B depicts another example embodiment of guidewire 102 with side looking capability. In this embodiment, signal line 124 is a conductive trace coupled along the length of elongate tubular member 104. Conductive trace 124 can include as many separate communication channels as needed to communicate with imaging device 103. Here, conductive trace 124 is covered by protective layer 720, which is preferably a polymer layer and can cover the exposed portion of trace 124 as depicted, or surround trace 124 as a sleeve.

Figure 8:
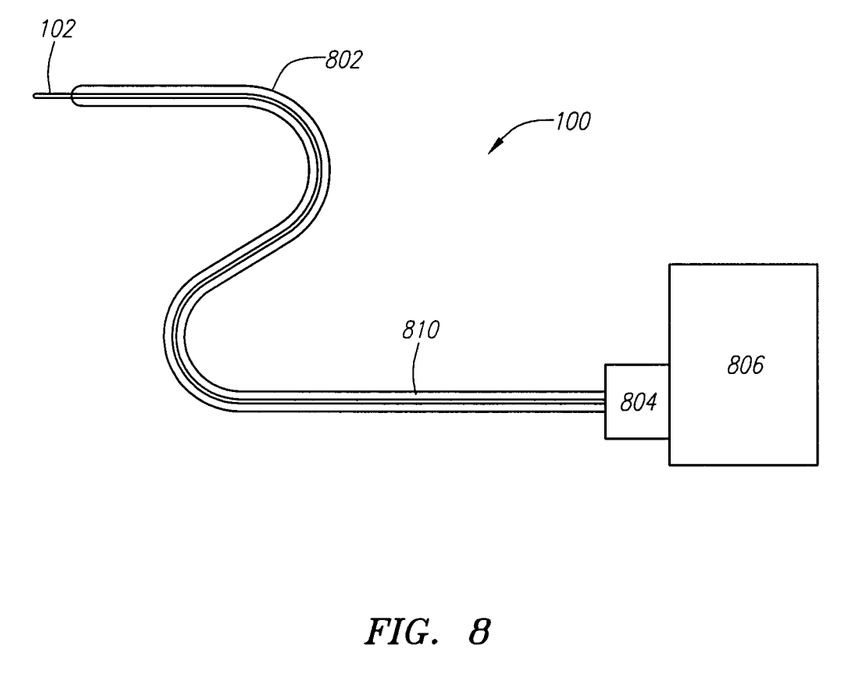
FIG. 8 is a schematic view depicting an example embodiment of a medical imaging system.

FIG. 8 depicts another example embodiment of medical imaging system 100. Here, system 100 includes guidewire 102, catheter 802, proximal connector 804 and image processing system 806. Catheter 802 preferably includes a lumen 810 configured to slidably receive guidewire 102. In this embodiment, lumen 810 is located within catheter 802 although the placement of lumen 810 can also be external to catheter 802 if desired. Catheter 802 and guidewire 102 are coupled with image processing system 806 by way of a common proximal connector 804, although separate proximal connectors for both catheter 802 and guidewire 102 can be used. Image processing system 806 is configured to process the image data collected by imaging devices 103 and/or 303 within guidewire 102 and display the resulting images for the user. In another embodiment, separate image processing systems (not shown) are used to process the images from guidewire 102 and catheter 802.

Figure 9:
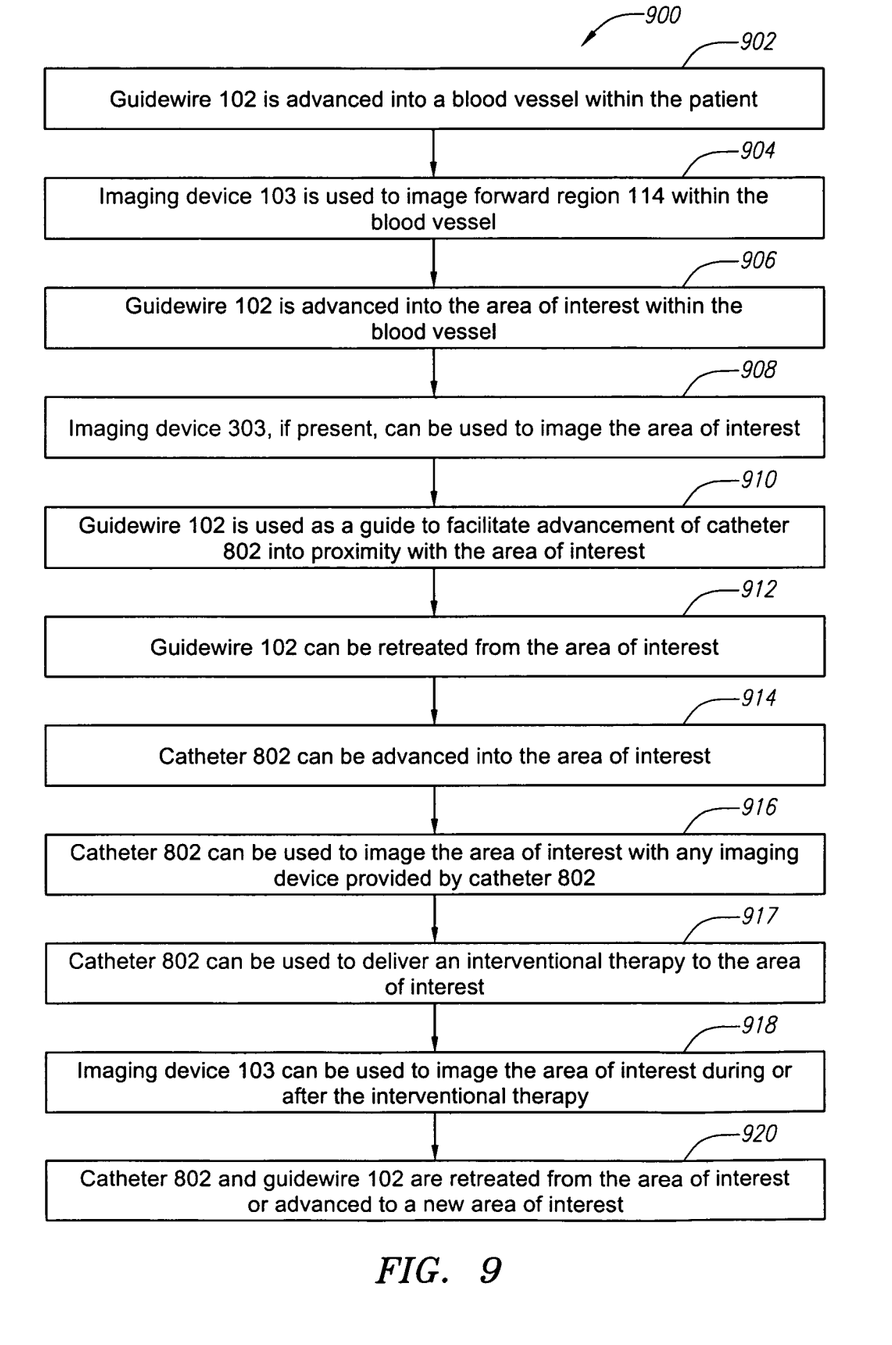
FIG. 9 is a block diagram depicting an example method of imaging with an example embodiment of the medical imaging system of FIG. 8.

FIG. 9 depicts an example method 900 of using guidewire 102 in a medical imaging procedure. It should be noted that method 900 is only one example of many medical imaging procedures in which guidewire 102 can be used. For instance, any of steps 906-920 can be omitted if desired, and the steps 902-920 can be performed in any order in accordance with the needs of the application.

At 902, guidewire 102 is advanced into a blood vessel within the patient and at 904, imaging device 103 is used to image forward region 114 within the blood vessel. Images of forward region 114 can be used for any purpose, such as for facilitating navigation through the blood vessel, determining the range to an area of interest within the blood vessel, such as an occlusion or other diseased tissue, characterizing the occlusion or diseased tissue region, evaluation of an interventional therapy during or after delivery of the therapy, general diagnostics of the interior of the blood vessel and any other desired purpose.

At 906, guidewire 102 is advanced into the area of interest within the blood vessel and, at 908, imaging device 303, if present, can be used to image the area of interest. At 910, guidewire 102 can be used as a guide to facilitate advancement of catheter 802 into proximity with the area of interest. At 912, guidewire 102 can be retreated from the area of interest to provide catheter 102 with more room to maneuver or operate. At 914, catheter 802 can be advanced into the area of interest and, at 916, catheter 802 can be used to image the area of interest with any imaging device provided by catheter 802. At 917, catheter 802 can be used to deliver an interventional therapy to the area of interest. As used herein, interventional therapy refers to any non-imaging method performed in the blood vessel to effect the blood or surrounding tissue. Examples of interventional therapies include, but are not limited to: tissue ablation; drug delivery; delivery of fluids (e.g., radioactive dyes etc.) to aid in imaging procedures; and delivery of an occlusion device such as a balloon, stent etc. At 918, imaging device 103 can be used to image the area of interest during or after the interventional therapy. At 920, catheter 802 and guidewire 102 are retreated from the area of interest or advanced to a new area of interest.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. As another example, the order of steps of method embodiments may be changed. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. An imaging system, comprising:
 a guidewire comprising a first imaging device, a second imaging device, and an elongate tubular member having a closed distal end, a distal region, a proximal region, an inner lumen, and a sonolucent end section located at the distal end, wherein the sonolucent end section has an outwardly curved front surface and a flat back surface that is perpendicular to a longitudinal axis of the elongate tubular member, wherein the first imaging device is located within the inner lumen and has a first surface coupled with the flat back surface of the sonolucent end section of the elongate tubular member and is configured to image a region located at least partially distal to the elongate tubular member, and wherein the width of the distal region is 0.025 inches or less, and wherein the elongate tubular member comprises
  a floppy member disposed over the distal region, the floppy member defining a plurality of apertures configured and arranged to increase flexibility of the distal region; and
  an outer layer disposed over the floppy member, the outer layer covering the plurality of apertures such that the plurality of apertures are not exposed to an environment external to the guidewire;
 wherein the second imaging device is coupled radially about a longitudinal portion of the elongate tubular member and is configured and arranged to image a region to a side of the elongate tubular member, wherein the second imaging device is disposed over a portion of the floppy member and beneath the outer layer, and wherein a signal line is electrically coupled to the second imaging device, the signal line extending from the second imaging device, through one of the plurality of apertures defined in the floppy member, and along the inner lumen to the proximal region of the elongate tubular member.

2. The imaging system of claim 1, wherein the distal end is configured as a matching layer.

3. The imaging system of claim 2, wherein the distal end is configured as a cap coupled with the elongate tubular member.

4. The imaging system of claim 3, wherein the first imaging device is coupled with the sonolucent end section of the elongate tubular member by an adhesive layer, the adhesive layer being configured as a matching layer.

5. The imaging system of claim 2, wherein the distal region of the elongate tubular member is curved and configured to be relatively more flexible than the proximal region.

6. The imaging system of claim 5, wherein at least a portion of the distal region of the elongate tubular member is metallic and comprises a polymer cap located at the distal end, the first imaging device being coupled to the polymer cap.

7. The imaging system of claim 1, wherein the width of at least a portion of the distal region is 0.018 inches or less.

8. The imaging system of claim 1, further comprising a catheter, wherein the inner lumen of the elongate tubular member is a first inner lumen and the catheter comprises a second inner lumen configured to slidably receive the guidewire.

9. The imaging system of claim 1, wherein at least one of the first or second imaging device is a transducer array.

10. An imaging guidewire, comprising:
 an elongate tubular member having a distal end, a distal region, a proximal region and an inner lumen, wherein the elongate tubular member comprises
  a floppy member disposed over the distal region, the floppy member defining a plurality of apertures configured and arranged to increase flexibility of the distal region, and
  an outer layer disposed over the floppy member, the outer layer covering the plurality of apertures such that the plurality of apertures are not exposed to an environment external to the guidewire;
 a first imaging device configured to image in a direction that is parallel to a length of the elongate tubular member at a location along the length of the elongate tubular member where the first imaging device is disposed, wherein the first imaging device is configured to image a region located at least partially distal to the elongate tubular member, wherein the width of the distal region is 0.025 inches or less, and wherein the first imaging device is located proximal to the distal end of the elongate tubular member such that at least one of the plurality of apertures is disposed distal to the first imaging device; and
 a second imaging device located proximal to the first imaging device and coupled radially about a longitudinal portion of the elongate tubular member and is configured and arranged to image a region to a side of the elongate tubular member, wherein the second imaging device is disposed over a portion of the floppy member and beneath the outer layer, and wherein a signal line is electrically coupled to the second imaging device, the signal line extending from the second imaging device, through one of the plurality of apertures defined in the floppy member, and along the inner lumen to the proximal region of the elongate tubular member.

11. The imaging guidewire of claim 10, wherein the first imaging device is located within the inner lumen and is coupled with a matching layer.

12. The imaging guidewire of claim 11, wherein the distal end of the elongate tubular member comprises a polymer cap.

13. The imaging guidewire of claim 11, wherein the distal region of the elongate tubular member is curved and configured to be relatively more flexible than the proximal region.

14. The imaging guidewire of claim 13, wherein at least a portion of the distal region of the elongate tubular member is metallic.

15. The imaging guidewire of claim 14, wherein the outer layer disposed over the floppy member comprises a thrombolytic agent.

16. The imaging guidewire of claim 14, wherein the outer layer disposed over the floppy member comprises a lubricious material.

17. The imaging guidewire of claim 10, wherein the elongate tubular member is configured to slide within a catheter lumen.

18. The imaging guidewire of claim 10, wherein the first imaging device is a transducer array.

19. The imaging guidewire of claim 10, wherein the first imaging device is coupled with a sonolucent section that extends radially across the inner lumen and is configured to support the imaging device.

20. The imaging guidewire of claim 19, wherein the first imaging device is coupled with the sonolucent section by an adhesive layer, the sonolucent section and adhesive layer each being configured as a matching layer.

21. The imaging guidewire of claim 10, further comprising a conductive trace coupled with the first imaging device and located along a portion of the elongate tubular member, wherein the conductive trace is covered by a protective layer.

22. The imaging guidewire of claim 10, further comprising a conductive trace coupled with the first imaging device and located along a portion of the elongate tubular member, wherein the conductive trace is integrated into the elongate tubular member.

23. A method for medical imaging, comprising: inserting the guidewire of claim 10 into a blood vessel;
imaging a region of the blood vessel located at least partially distal to the guidewire with the first imaging device of the guidewire; and
imaging a region of the blood vessel located proximal to the first imaging device with the second imaging device of the guidewire.

24. The method of claim 23, further comprising:
identifying an area of interest located within the imaged region located at least partially distal to the guidewire; and
advancing a catheter over the guidewire to the area of interest, wherein the catheter is configured to perform an interventional therapy.

25. The method of claim 24, further comprising performing the interventional therapy at the area of interest.

26. The method of claim 25, further comprising imaging the area of interest during or after the interventional therapy.

27. The method of claim 23, further comprising:
advancing a catheter to an area of interest within the blood vessel prior to imaging the blood vessel, wherein the catheter is configured to perform an interventional therapy; and
performing the interventional therapy with the catheter.

28. The method of claim 24, further comprising imaging the area of interest with the second imaging device.

29. The method of claim 23, wherein imaging a region of the blood vessel comprises imaging an occlusion in the blood vessel.

30. The method of claim 23, further comprising:
identifying an area of interest located within the imaged region located at least partially distal to the guidewire;
advancing the guidewire to the area of interest; and
imaging the area of interest to characterize an occlusion within the area of interest.

31. The method of claim 30, further comprising:
advancing a catheter over the guidewire to the occlusion, the catheter configured to perform an interventional therapy; and
performing the interventional therapy on the occlusion.

32. The method of claim 31, further comprising imaging the area of interest during or after the interventional therapy.

33. The imaging system of claim 1, wherein the sonolucent end section comprises a polymer and the first imaging device is coupled with the sonolucent end section by an adhesive.

34. The imaging guidewire of claim 10, wherein the second imaging device comprises a cylindrical imaging device.

35. The imaging system of claim 1, wherein the floppy member is metallic.

36. The imaging system of claim 1, wherein the second imaging device is disposed proximal to the floppy member.

37. The imaging guidewire of claim 10, wherein the second imaging device is disposed proximal to the floppy member.

38. The imaging guidewire of claim 13, wherein at least a portion of the floppy member disposed proximal to the distal end is sonolucent.

39. The imaging guidewire of claim 38, wherein the first imaging device is configured and arranged to image through at least one bend in the guidewire.

40. The imaging guidewire of claim 10, wherein the first imaging device is located proximal to the distal end of the elongate tubular member such that the first imaging device is positioned closer to the proximal region of the elongate tubular member than to the distal end.

* * * * *